(12) United States Patent
Clift

(10) Patent No.: US 6,976,963 B2
(45) Date of Patent: Dec. 20, 2005

(54) APPARATUS AND METHOD FOR PRECISION VITAL SIGNS DETERMINATION

(76) Inventor: Vaughan L. Clift, 807 Noble Spring Rd., Houston, TX (US) 77062

(*) Notice: Subject to any disclaimer, the term of this patent is extended or adjusted under 35 U.S.C. 154(b) by 160 days.

(21) Appl. No.: 10/261,169

(22) Filed: Sep. 30, 2002

(65) Prior Publication Data

US 2004/0064054 A1  Apr. 1, 2004

(51) Int. Cl.[7] .............................. A61B 5/02; A61B 5/08
(52) U.S. Cl. .................... 600/484; 600/483; 600/485; 600/529
(58) Field of Search ................ 600/483, 484, 600/500–504, 507, 481, 476, 479, 473, 300, 600/301, 559

(56) References Cited

U.S. PATENT DOCUMENTS 5,673,692 A * 10/1997 Schulze et al. ............. 600/301
6,004,274 A    12/1999 Nolan et al.
6,454,718 B1 * 9/2002 Clift ........................... 600/483

FOREIGN PATENT DOCUMENTS

WO    WO 9923941 A1 * 5/1999   ......... A61B 5/0205

* cited by examiner

Primary Examiner—Robert L. Nasser
Assistant Examiner—N. Natnithithadha
(74) Attorney, Agent, or Firm—Harish Dhingra; Dhingra & Associates

(57) ABSTRACT

Apparatus and techniques are provided for precise measuring and monitoring of certain vital signs of patients that have been difficult to measure especially in emergency situations. Sensor may be used for detecting contraction and expansion in the vascular bed of the lining tissue of the external auditory canal during a cardiac cycle to obtain a better indication of certain physiological parameters. Such a signal generally may be superimposed with an additional signal that is primarily due to breathing activity of the patient. Based on various scenarios different sensors may be used to determine the signal due to breathing activity and thus the physiological parameter of interest may be derived. The signal corresponding to the physiological parameter of interest, for example, blood pressure may then be used to monitor the vital signs or control other medical equipment.

6 Claims, 2 Drawing Sheets

APPARATUS AND METHOD FOR PRECISION VITAL SIGNS DETERMINATION

CROSS-REFERENCE TO RELATED APPLICATIONS

Not Applicable.

STATEMENTS REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Field of the Invention

The present invention generally relates to determination and monitoring of vital signs and more particularly relates to accurate determination and monitoring of vital signs by detecting contraction and expansion in the vascular bed of the lining tissue of the external auditory canal.

2. Description of the Related Art

As described in the U.S. Pat. No. 6,454,718, issued to the applicant, the signal present at the external auditory meatus and canal, "the external auditory canal", is a combination of blood pressure and respiratory signals. The respiratory signal itself is produced by simultaneous pressure events in the structures of the head and neck. These include the transmission of pressure changes in the naso-pharynx and trachea, the expansion and contraction of intrathoracic blood vessels and cardiac volume and changes in muscle tone in the accessory muscles of respiration.

The process of breathing is a complex process involving, "ventilation" or movement of gases, "diffusion" or transport of gases across the alveolar epithelium and perfusion movement of blood into and out of the lung. Pathology effecting one or all of these areas can and does occur with the net effect being short of breath. However, different therapeutic interventions require a clear understanding of the relative decrease in each of these areas and this require different diagnostic sensors or approaches to be used simultaneously.

In fact, application of any therapy without understanding what is going on with each area can be detrimental if not fatal. Even the application of oxygen can lead to fatal consequences through the suppression of hypoxic drive and CO2 retention, if the pathology is not understood.

In true physics terms, air is not sucked into the lungs, but is pushed in by the atmospheric pressure when the relative intra thoracic pressure is lowered below the point where it overcomes airways resistance. In mechanical terms, the muscles supporting the rib cage and the diaphragm itself contract in such a way as to increase the volume of the rigid chest wall. The accessory muscles lift and separate the ribs like a bellows and the diaphragm pulls down toward the abdomen. The pliable, sponge-like lung tissue expands to fill the vacuum produced and air is drawn into the lungs through airways.

Understanding this mechanism helps to explain the various pathologies that affect a patient who is having trouble breathing. At the outside, failure of the muscles to contract as a result of fatigue or neurological injury prevents the expansion of the chest cavity. Several conditions can be lead to paralysis of the diaphragm and the flail muscle moves passively in and out as the patient breathes. Only if the accessory muscles of respiration, such as the intercostals, trapezius and pectorals can expand the chest cavity to overcome the loss of the diaphragm contribution will the patient be able to survive.

Expansion of an intra-abdominal contents, such as with gastric outflow obstruction, mechanically restricts movement of the chest wall and pushes the diaphragm high into the chest cavity. At extremes, this prevents generation of the negative intrathoracic pressure and the patient suffocates.

A multiple rib fracture produces a flail segment of chest wall which can move in and out with respiration, though usually tethered by muscle and tendon, if the ribs are broken in enough places there is no rigid structure to produce the vacuum against and the patient must receive positive pressure ventilation to survive.

If the lung itself is less compliant such as with pneumonia or cardiac failure then the work of expanding the lung is increased. In addition, if the airways are narrowed such as with asthma, the pressure required to produce the same degree of air movement is markedly greater.

BRIEF SUMMARY OF THE INVENTION

Techniques for precision determination and monitoring of important physiological parameters are illustrated. In one embodiment a sensor senses a first signal corresponding to a physiological parameter that is superimposed with an undesired signal component, by detecting contraction and expansion in the vascular bed of the lining tissue of the external auditory canal during a cardiac cycle. Another sensor or device senses a second signal corresponding to the undesired signal component. The first signal and the second signal are then appropriately combined to obtain a third signal corresponding to the physiological parameter of interest.

In another embodiment of the technique, a sensor senses a first signal corresponding to a physiological parameter that is superimposed with an undesired signal component, by detecting contraction and expansion in the vascular bed of the lining tissue of the external auditory canal during a cardiac cycle. Another sensor or device senses a second signal corresponding to the undesired signal component. The first signal and the second signal are then appropriately combined to obtain a third signal corresponding to the physiological parameter of interest. This third signal may then be used to monitor the vital signs of the patient or may be used to control other medical equipment.

In a still another embodiment of the technique, a sensor senses a first signal corresponding to a blood pressure representing diastolic and systolic blood pressure that is superimposed with an undesired signal component, by detecting contraction and expansion in the vascular bed of the lining tissue of the external auditory canal during a cardiac cycle. Another sensor or device senses a second signal corresponding to the undesired signal component. The first signal and the second signal are then appropriately combined to obtain a third signal corresponding to the diastolic and systolic blood pressure. By determining variation of the diastolic and systolic blood pressure vital signs one can determine the phenomenon known as paradox.

In still another embodiment an apparatus for precision determining and monitoring of the vital signs is provided. A first sensor senses a first signal corresponding to contraction and expansion in the vascular bed of the lining tissue of the external auditory canal during a cardiac cycle. A second sensor senses a second signal representing effect on the physiological parameter due to respiratory cycle. A processor coupled to the first sensor and the second sensor appropriately combines the first signal and the second signal to generate a third signal corresponding to the physiological parameter of interest.

BRIEF DESCRIPTION OF THE SEVERAL VIEWS OF THE DRAWINGS

A better understanding of the present invention can be obtained when the following detailed description of some embodiments is considered in conjunction with the drawings of the above noted application and the following drawings in which:

FIG. 1a is a timing diagram illustrating a signal corresponding to a physiological parameter with a superimposed signal corresponding to an undesired signal in an exemplary technique according to one example embodiment.

FIG. 1b is a timing diagram illustrating an undesired signal component relating to breathing cycle that is part of the signal shown in FIG. 1a.

FIG. 1c is a timing diagram illustrating a signal obtained by appropriately combining signals of FIG. 1a and of FIG. 1b.

DETAILED DESCRIPTION OF THE INVENTION

Figure 1:
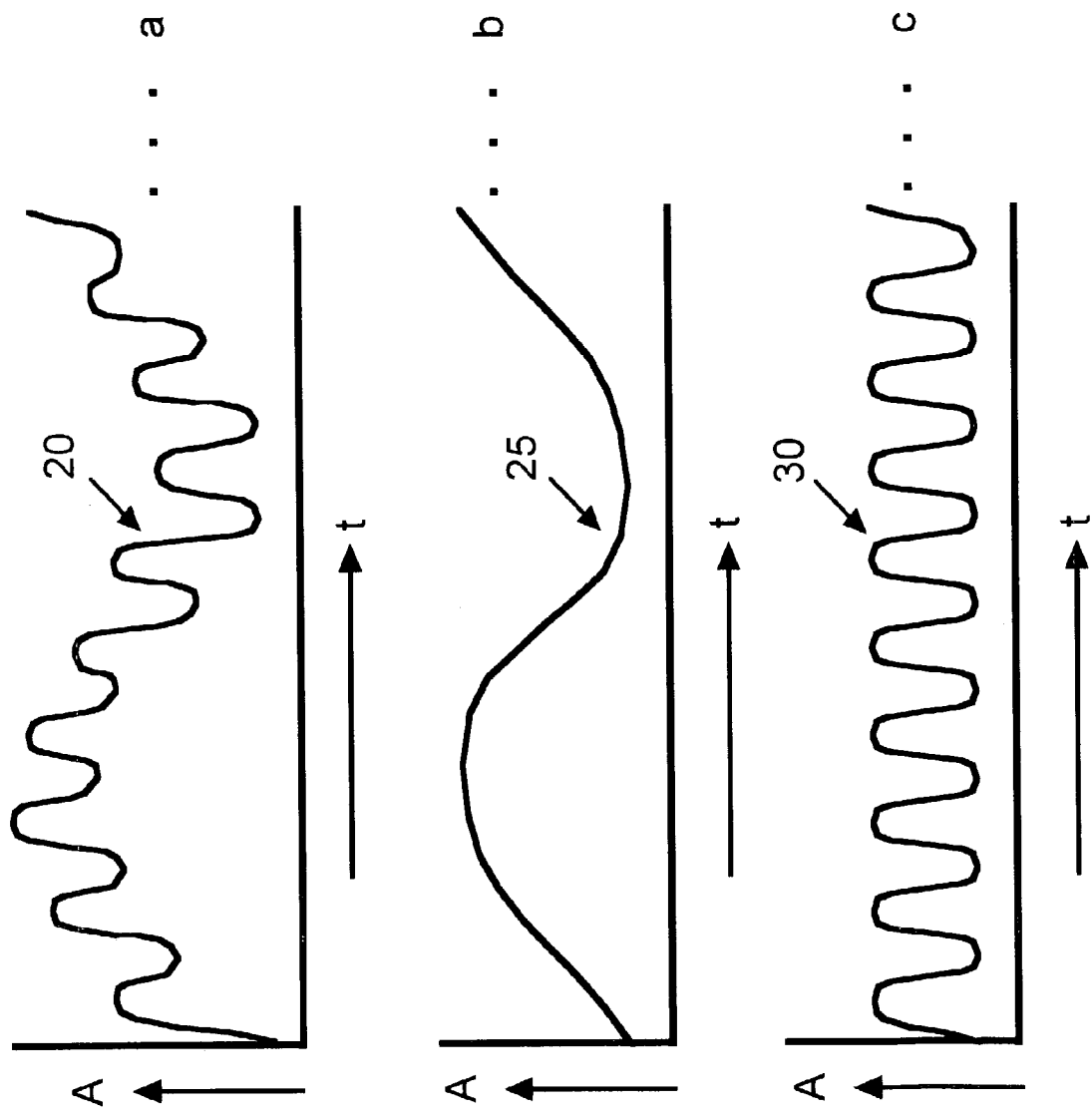

The observation of changes in thoracic pressure is well noted in the medical literature and is a standard clinical sign. However, prior to this invention, it could only be detected by a careful observation of neck veins and by careful auscultation of blood pressure by a highly trained observer. The observation of neck veins is extremely difficult in the recumbent or obese patient and is largely not done. Determination of "paradox" by blood pressure cuff requires careful auscultation, noting when the pulse sound first appears in comparison to inspiration and expiration and then independently of breathing. In a noisy emergency setting with a distressed and moving patient this method is unreliable.

Determination of respiratory rate is commonly done using impedance plethysmography. In this method the chest leads have a high frequency AC signal applied to them. The volume of tissue the signal passes through alters the passage and attenuation of this signal through the chest. However, it is affected not only by the volume but also by the shape of the chest. It is therefore possible, for there to be little or no airflow and there is no technique to measure a "respiratory rate" of such patients. Such is the case with severe obstruction of the airways, whereby the chest changes shape but not overall volume and the air does not move in or out.

Other factors such as patient movement and pleural fluid also interfere with impedance plethysmography methods.

Therefore, an ability to determine the swings in thoracic pressure associated with the breathing cycle would be valuable. In addition to other measured and clinical parameters it may even be diagnostic. By the way of example, the association of lowered blood oxygen saturation, increased respiratory rate, and increased swings in thoracic pressure would indicate airways obstruction such as reactive airways diseases like asthma. In fact, response to medication could be monitored objectively by how much the bronchodilator reduced the swings in thoracic pressure required to ventilate the lung.

A more marked swing on inspiration than expiration would imply a flap or valve like obstruction as occurs with layringo tracheo bronchitis or "croup", epiglotittis and trauma to the head and neck.

Conversely, a reduction of the normal thoracic pressure swing expected in the presence of observed respiratory effort would imply intra thoracic, pathology such as pneumothrax, hemothorax or pleural effusion. The likelihood of each will be determined by the rate of onset and other clinical factors. However, this observation, not only leads to selection of intervention (such as draining the air or fluid) but a monitor of the need for positive airway pressure or ventilation.

Thus, there is a need for an integrated approach, and further the addition of novel sensing technique which can sense breathing in above described difficult situations will greatly enhance a care givers understanding of the underlying state of the respiratory and cardiovascular system and permit safer and improved medical care.

Exemplary techniques described herein allow the changes in thoracic pressure to be measured continuously and independently of any applied cuff. In one exemplary embodiment of the technique a sensor, described in the above referenced PCT application, is placed on the ears like a headset that measures the pressure wave in the expanding and contacting vascular bed. Alternatively, the sensor may be placed inside the ear canal and other locations that would be apparent to those skilled in the art. Referring to FIGS. 1a, 1b, and 1c, in one example embodiment of a technique, is a combination of a first signal 20 corresponding to a physiological parameter, for example blood pressure, and a second signal 25 corresponding to an undesired signal, for example, intra thoracic pressure. For useful information to be extracted from the first signal, it is advantageous to separate the first signal 20 into its components the second signal 20 and the third signal 30 corresponding to the desired physiological parameter, for example, blood pressure. The second signal 25 may require phase correction due to different time of travel as well as may require amplitude correction due to additional media travel as would be well known to those skilled in the art. The first signal 20 and the second signal 25 may then be combined, for example, by subtracting the second signal from the first signal to obtain the third signal corresponding to the blood pressure. Several variations of the described technique may be developed to extract any desired physiological parameter from a combined signal like the first signal 20. Further, the first signal 20 and the second signal 25 may be applied with additional corrections based on their travel times and characteristics of the media.

There are several alternative techniques for implementing the technique illustrated above using separate but related information about the signal derived from one of a plurality of sensors, including but not limited to, for example: pulse oximetry, ECG, impedance plethysmography, capnography, nasal airflow, EMG, oxygen sensor based breath oximetry, chest wall movement, thermography, auscultation, and other means that would be apparent to those skilled in the art.

By way of example, one example embodiment uses the pulse oximetry signal obtained from the tissues of the external pinna adjacent to the pressure sensor. In this embodiment, it is known that the timing, phases, shape and features of the saturation waveform relate directly to the characteristics of the pressure waveform. This is because the changes in saturation seen in the pulse oximeter waveform reflect the influx of oxygenated blood into the region. The same influx of blood causes or is caused by, the pressure changes in the vessel. Therefore, the initiation of positive increase in the saturation occurs in phase with the increase in pulse pressure, the peak, dichrotic notch and dissipation of the waveform also correlate with changes in the pressure waveform.

This is because the signals are produced by the same physical event. Even if the oximetry probe is placed more peripherally, many of the characteristics can be used the same way if allowance is made for delay and, as noted above, some modification of the waveform.

The timing of the signal from the pulse oximeter and the duration of the waveform can be used to correct the signal from the pressure sensor due to poor coupling or placement. This can be done through alerting an operator or through an appropriate algorithm, which modifies the pulse waveform scale or offset or shape to more correctly reflect the pulse pressure. In addition, the timing, duration, waveform shape and amplitude can be used as a reference for subtraction of the pulse pressure signal from the combined signal; the respiratory pressure changes having little or no effect on the saturation waveform.

The respiratory signal can be reconstructed from the new waveform. This reconstructed respiratory waveform can further be used by inverting it and subtracting it from the original combined waveform to produce a pulse pressure waveform missing the respiratory pressure change effect.

A similar approach can be used in a yet another embodiment where the ECG signal timing is used to obfuscate a defined period on the combined waveform after adjustment for any time delay. Due to transit time the pressure waveform lags behind the ECG signal and with appropriate calibration can be used to identify or hide the cardiac waveform. The same reconstruction of respiratory waveform can be performed and the same subtraction of that waveform from the combined signal as described previously.

Still another embodiment uses a pulse waveform produced by Doppler flow sensor attached to the carotid artery in the neck or measuring flow in the vessels and capillary bed in the ear. A signal waveform is generated by the reflection of sound waves off blood cells traveling in the vessels of the neck. The auscultation can be more complicated in that depending on the location of the microphone, a respiratory signal produced by turbulence in the trachea and bronchi, rather than a cardiac cycle, may be detected. This breath sound may be used to separate the signals as with the nasal flow sensor or capnograph described below.

Any modality including induced body motion, changes ocular pressure and visible pulsation that accurately identifies the timing of the cardiac cycle can be used to separate the waveform in this way. The more information available about the pulse waveform the more accurately the subtraction and separation can be performed. Conversely, comparison of the pulse waveform from the pressure sensing method and the pulse waveform from any other source can identify errors in that sensor. By way of example, the shape and limits of the pressure waveform may be compared to a known set of standards electronically or within software to attain a degree of certainty that it is a pressure signal. Once established, this signal could be used to validate an ECG signal, pulse oximeter signal, blood flow signal or other. Even simply determining that the two signals are not in phase or proportion may indicate an error state to an operator.

In a further exemplary embodiment the respiratory signal is separated from the combined signal in another way. In this embodiment, a separate reference for the respiratory component is obtained from a separate sensor such as a flow sensor placed at the external nare, from the chest wall movement signal that may be obtained from a breath sampling capnograph once allowance made for delayed processing. This signal is then used to indicate respiratory changes and subtract them from the combined signal. Due to the slower, lower amplitude signal that may be the respiratory component, subtraction be this method may be less accurate however, a significant disparity between the signal such as the pressure component and a breath flow measurement may indicate significant pathology such as airway obstruction described previously.

Figure 3:
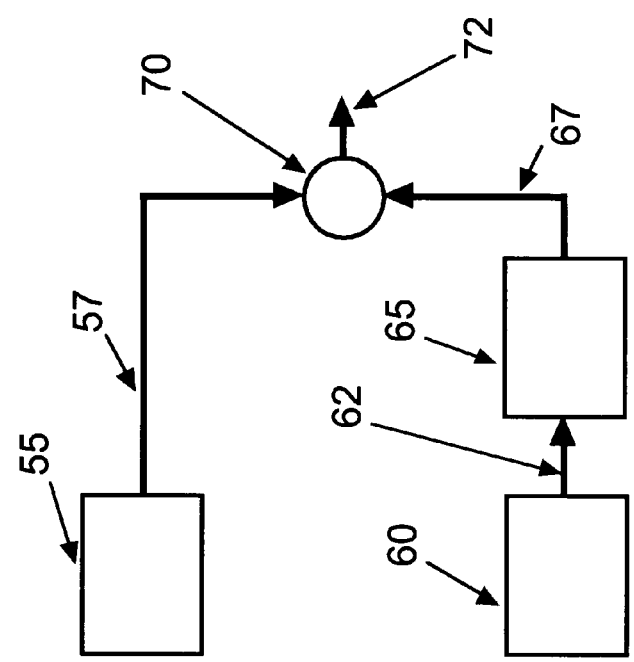
FIG. 3 is a block diagram of an apparatus for precision measurements and monitoring of vital signs according to one example embodiment.

Referring to FIG. 3 is shown a block diagram of an apparatus 50 for precision measurements and monitoring of vital signs according to one exemplary embodiment. A sensor 55 senses a first signal 57 that corresponds to the contraction and expansion in the vascular bed of the lining tissue of the external auditory canal during a cardiac cycle. The first sensor is essentially a pressure sensor that may be a piezoelectric pressure transducer, a strain gauge transducer, or a ceramic pressure transducer appropriately adapted to sense the contraction and expansion in the vascular bed of the lining tissue of the external auditory canal. The first signal 57 may be used to derive systolic blood pressure, diastolic blood pressure, pulse rate, pulse pressure or any combination of these parameters. A second sensor 60 senses a second signal 62 representing effect on the physiological parameter due to the respiratory cycle. The second sensor 60 may be an oximeter, an impedance plethysmograph, or a capnograph used to measure the second signal 62. The second signal 62 may also be generated by measurement of nasal flow, using EMG, using oxygen sensor based breath oximetry, using chest wall movement, using pressure across the tympanic membrane, using ultrasonic blood flow measurement, using thermography, or using auscultation. The second signal may be corrected for phase or time delay, and or amplitude adjustment based on the application by a device 65 to generate an adjusted second signal 67. Signal phase adjustment and signal amplitude device are common and well known to those skilled in the art. The first signal 57 and the second signal 62 or the adjusted second signal 67 may then be combined together by a processor 70 to obtain a third signal 72 corresponding to the physiological parameter of interest. The third signal 72, corresponding to blood pressure, pulse rate, pulse pressure or any combination thereof, may thus be used to monitor the vital signs of the patient. The third signal 72 may also be used to control a medical device, for example, a counterpulsation device or a defibrillator device. The exemplary technique illustrated may be used to generate signals corresponding any other vital signs necessary in variety of medical scenarios as would be within the skills of those with skilled in the art.

Figure 2:
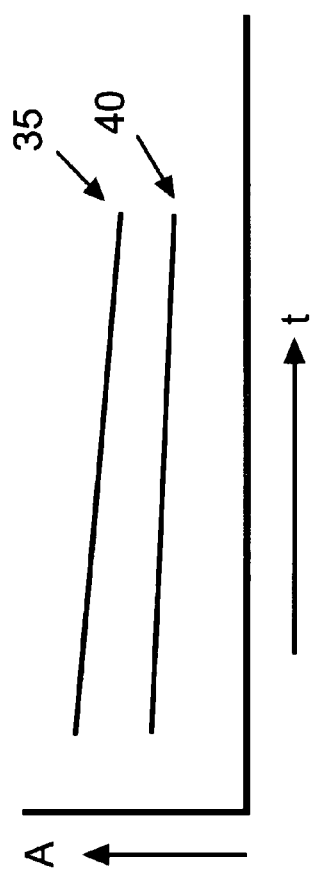
FIG. 2 is a timing diagram of the variation of the diastolic blood pressure and the systolic blood pressure with the breathing cycle to determine the paradox according to one example embodiment.

Determination of "Paradox" as a Useful Diagnostic Parameter:

The variation in mean or systolic blood pressure in the carotid artery produced by changes in the thoracic pressure in within relatively narrow limits in a healthy population, usually between 5 and 10 mmHg on the BP cuff. This is independent of the blood pressure itself but changes proportionately with age and vascular compliance. Referring to FIG. 2, a variation of diastolic blood pressure 35 and a variation of a systolic blood pressure 40 with time are shown. It is therefore possible by comparing the pressure changes noted on top of the blood pressure change and comparing this to expected values of the diastolic blood pressure 35 and the systolic blood pressure 40, to quickly identify an out of range respiratory pressure swing. As described previously, this could be used to indicate to the operator possible pathology or bronchodilators.

Pulse Pressure Monitoring

Physiological autonomic changes associated with beat-to-beat variation have long been recognized as makers of autonomic function, specific patterns or loss of beat-to-beat variation are associated with various autonomic dysfunctions and states. The technique disclosed herein provides a method wherein such measurement can be made with minimal impact to the patient and in an ambulatory setting. In many settings, pulse pressure which is the difference between systolic and diastolic blood pressure can provide valuable information with regard to a patients well being. This may be further enhanced by comparison of the pulse pressure against a BP cuff placed on the arm. A lower than expected pulse pressure may be indicative of arterial stenosis if it is a chronic state or increased intracranial pressure if it is an acute change such as with meningitis or intracranial bleed.

In addition the pulse pressure waveform lends itself to a smaller more portable unit. Such a unit may connect by wire or alternatively transmit the signal to remote unit. Such transmission may be by way of RF or infrared transmission or directly through the body.

Determination of Effective CPR

One unique feature of the ear pulse pressure method disclosed herein is the ability to monitor pulse pressure changes produced by cardio pulmonary resuscitation or pressure to the chest. This method would be a valuable tool during the emergency care of a critical ill patient and provide a hitherto unavailable reference to the effectiveness of resuscitation measures. Previously the only such marker was physical palpation of a large vessel usually the femoral artery going to the leg. This method provides a marker of the perfusion pressure into the head and brain and when couple to concurrent oxygen saturation measurement would provide a valuable indicator of the efficacy of CPR efforts.

The foregoing disclosure and description of the preferred embodiment are illustrative and explanatory thereof, and various changes in the components, elements, configurations, and signal connections, as well as in the details of the illustrated apparatus and construction and method of operation may be made without departing from the spirit and scope of the invention and within the scope of the claims.

What is claimed is:

1. A method comprising:
   a. sensing a first signal corresponding to a blood pressure superimposed with a signal component corresponding to a respiratory cycle by detecting contraction and expansion in the vascular bed of the lining tissue of the external auditory canal during a cardiac cycle;
   b. sensing a second signal representing the signal component corresponding to the respiratory cycle; and
   c. removing the second signal from the first signal to derive a third signal corresponding to the blood pressure.

2. The method as in claim 1, wherein the blood pressure comprises of a diastolic blood pressure and a systolic blood pressure.

3. The method as in claim 2, further comprising of determining a blood pressure paradox.

4. The method as in claim 3, wherein the blood pressure paradox comprises a time variation of the systolic blood pressure with changes in a respiratory cycle.

5. The method as in claim 3, wherein the changes in the respiratory cycle comprise changes during breathing in and changes during breathing out.

6. The method as in claim 3, wherein the blood pressure paradox is used as an indicator of a disease state.

* * * * *